(12) United States Patent
Rabe

(10) Patent No.: US 7,128,725 B2
(45) Date of Patent: Oct. 31, 2006

(54) ANKLE BRACE

(76) Inventor: David Rabe, 29 Overlook Rd., Chatham, NJ (US) 07928

(*) Notice: Subject to any disclaimer, the term of this patent is extended or adjusted under 35 U.S.C. 154(b) by 25 days.

(21) Appl. No.: 10/687,455

(22) Filed: Oct. 16, 2003

(65) Prior Publication Data
US 2005/0085755 A1 Apr. 21, 2005

(51) Int. Cl.
A61F 5/00 (2006.01)

(52) U.S. Cl. ............... 602/27; 602/23; 602/28; 602/29

(58) Field of Classification Search ........... 602/5, 602/23, 27–29, 65–66; 2/22; 128/869, 882, 128/892–894; 36/89
See application file for complete search history.

(56) References Cited

U.S. PATENT DOCUMENTS

| 674,066 | A | * | 5/1901 | Mitchell | 602/65 |
|---|---|---|---|---|---|
| D270,284 | S | | 8/1983 | Lindh et al. | D24/64 |
| 4,862,900 | A | * | 9/1989 | Hefele | 602/27 |
| 5,219,324 | A | | 6/1993 | Hall | 602/28 |
| D338,066 | S | | 8/1993 | Baron | D24/192 |
| 5,425,701 | A | * | 6/1995 | Oster et al. | 602/23 |
| 5,445,602 | A | * | 8/1995 | Grim et al. | 602/27 |
| 5,472,411 | A | * | 12/1995 | Montag et al. | 602/23 |
| 5,501,659 | A | * | 3/1996 | Morris et al. | 602/27 |
| 5,507,720 | A | | 4/1996 | Lampropoulos | 602/27 |
| 5,637,077 | A | | 6/1997 | Parker | 602/8 |
| D388,174 | S | | 12/1997 | Stano | D24/192 |
| 5,720,715 | A | * | 2/1998 | Eriksson | 602/65 |
| 5,741,222 | A | * | 4/1998 | Fiore | 602/27 |
| 5,817,041 | A | * | 10/1998 | Bader | 602/23 |
| 5,853,380 | A | * | 12/1998 | Miller | 602/27 |
| D412,581 | S | | 8/1999 | Brennan | D24/192 |
| 5,957,871 | A | | 9/1999 | Darcey | 602/12 |
| 6,019,741 | A | | 2/2000 | Prieskorn | 602/5 |
| 6,155,997 | A | * | 12/2000 | Castro | 602/27 |
| D436,177 | S | | 1/2001 | Miller | D24/192 |
| 6,245,035 | B1 | * | 6/2001 | Schrijver | 602/27 |
| 6,394,971 | B1 | * | 5/2002 | Slautterback et al. | 602/27 |
| 6,443,919 | B1 | | 9/2002 | Castro | 602/27 |
| 6,652,474 | B1 | * | 11/2003 | Quinn et al. | 602/21 |
| 6,767,332 | B1 | * | 7/2004 | Pardue et al. | 602/27 |
| D499,185 | S | * | 11/2004 | Rabe | D24/192 |
| 2002/0029009 | A1 | | 3/2002 | Bowman | |
| 2003/0171707 | A1 | | 9/2003 | Bodenschatz et al. | 602/65 |
| 2004/0015113 | A1 | * | 1/2004 | Gardner et al. | 602/27 |
| 2004/0019307 | A1 | * | 1/2004 | Grim et al. | 602/27 |

OTHER PUBLICATIONS

"Depend on Success," pamphlet distributed by Custom Footwear, Inc., Mesa, AZ and Tower Orthopedic Designs, Inc., Pittsburgh, PA, describing the Arizona AFO.

"Don't Just Live With the Pain," pamphlet describing the Arizona AFO.

* cited by examiner

Primary Examiner—Henry Bennett
Assistant Examiner—Amanda Wieker
(74) Attorney, Agent, or Firm—McCarter & English, LLP

(57) ABSTRACT

A rear entry ankle brace for providing support and stability to an ankle includes a rigid internal support member covered on both sides by a soft durable material. The ankle brace is secured about a leg with an adjustable strap. A flexible heel is provided for facilitating walking.

19 Claims, 7 Drawing Sheets

ANKLE BRACE

BACKGROUND OF THE INVENTION

1. Field of the Invention

The present invention relates to an ankle brace device, and specifically to an ankle brace that is easily put on and minimizes interference with walking.

2. Related Art

Ankle orthoses have become a standard treatment for orthopedic foot and ankle problems. Most are bulky and entirely rigid. Typically, a plurality of straps are required for attachment about the foot and ankle. These devices are cumbersome and time-consuming to apply and diminish proprioception while ambulating because the heel is covered by the device. Further, these devices are difficult to wear with standard footwear, leaving an individual self-consciously wearing only one shoe and an unsightly brace.

What is needed, but has not yet been provided, is an ankle brace which is easy to put on, which provides necessary support, which provides a comfortable fit, and which allows for easy walking.

SUMMARY OF THE INVENTION

The present invention provides an ankle brace having a rigid member that extends under a foot and up along sides of an ankle and lower leg. Inner and outer layers surround the rigid member and form a body. The body has a foot portion including a forward edge defining a toe aperture, a footbed, and a leg portion joined to the foot portion, the leg portion including an upper edge, and rear edges extending from the upper edge to the footbed. The foot portion covers the top of the foot and the leg portion covers the front of the lower leg. A fastening strap is connectable about the leg portion to retain the brace on the foot, ankle and leg of the individual. A flexible heel portion extends from the footbed. A cushion layer can be provided between the inner layer and the rigid member.

The present invention also provides a method for treating an ankle injury using the ankle brace of the invention. The method comprises custom forming a rigid member, incorporating the rigid member in a body having inner and outer layers, inserting a foot, toes first, between rear edges of a leg portion of the body; inserting the toes through a toe aperture; placing the foot onto a footbed portion; fastening a strap about the leg portion to secure the ankle brace to a foot and leg; and wearing the ankle brace on the leg for a sufficient time to treat the injury. The method further includes allowing the heel to flex to facilitate walking.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

The ankle brace of the present invention is provided for stabilizing and/or treating the ankle for ankle injuries and conditions including posterior tibialis tendon dysfunction, Charcot ankle, Achilles tendon rupture and general ankle instability and derangement. The ankle brace can be custom made for each patient. The ankle brace provides support and stability, and controls the motion of an injured foot and ankle by encasing the dorsum of the foot. This ensures proper positioning in the device and better mediolateral control of the ankle and arch of the foot. The ankle brace intimately fits and conforms to the natural skeletal and muscular structure of the foot.

The ankle brace of the present invention is shown in FIGS. 1–7. The ankle brace is generally indicated in the FIGS. at 10. The ankle brace comprises a foot engaging portion and a leg engaging portion. The ankle brace 10 includes inner and outer layers forming a boot-shaped body 12 having an open toe, an open back and a flexible heel. A rigid support member 30 is positioned within the inner and outer layers. The rigid support is preferably in the form of a single integral member extending under the foot to form a footbed portion, and extending up along the sides of the ankle and lower leg.

Figure 1:
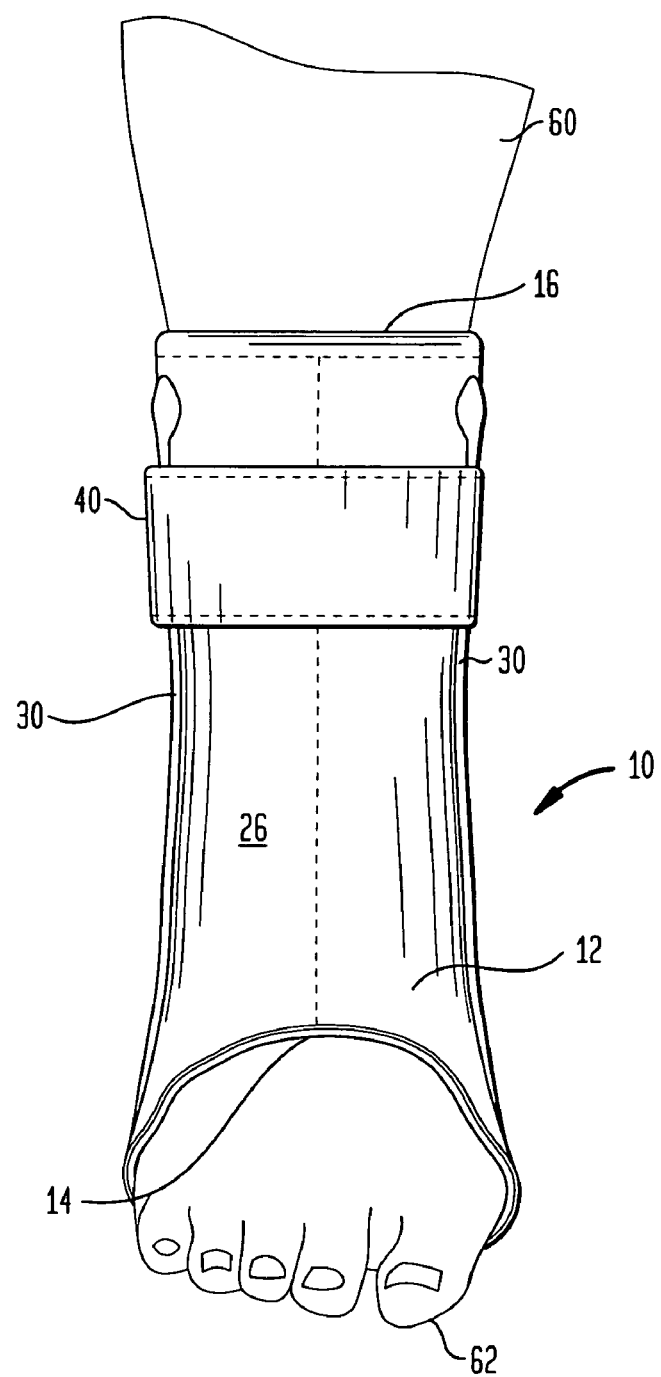
FIG. 1 is a front view of the ankle brace of the invention on a foot.

As shown in FIG. 1, a foot, ankle, and leg 60 are placed into the ankle brace 10. The body 12 has a forward edge 14 through which toes 62 of a foot extend. The body includes a foot portion and a leg portion. The foot portion is sized to receive and surround a foot. The foot portion includes a footbed. The leg portion, as will be described, covers the lower front portion of the leg and partially surrounds the leg. The leg portion has an upper edge 16. Strap 40 secures the ankle brace to the foot and leg. Outer layer 26 is positioned over the rigid support member 30.

Figure 2:
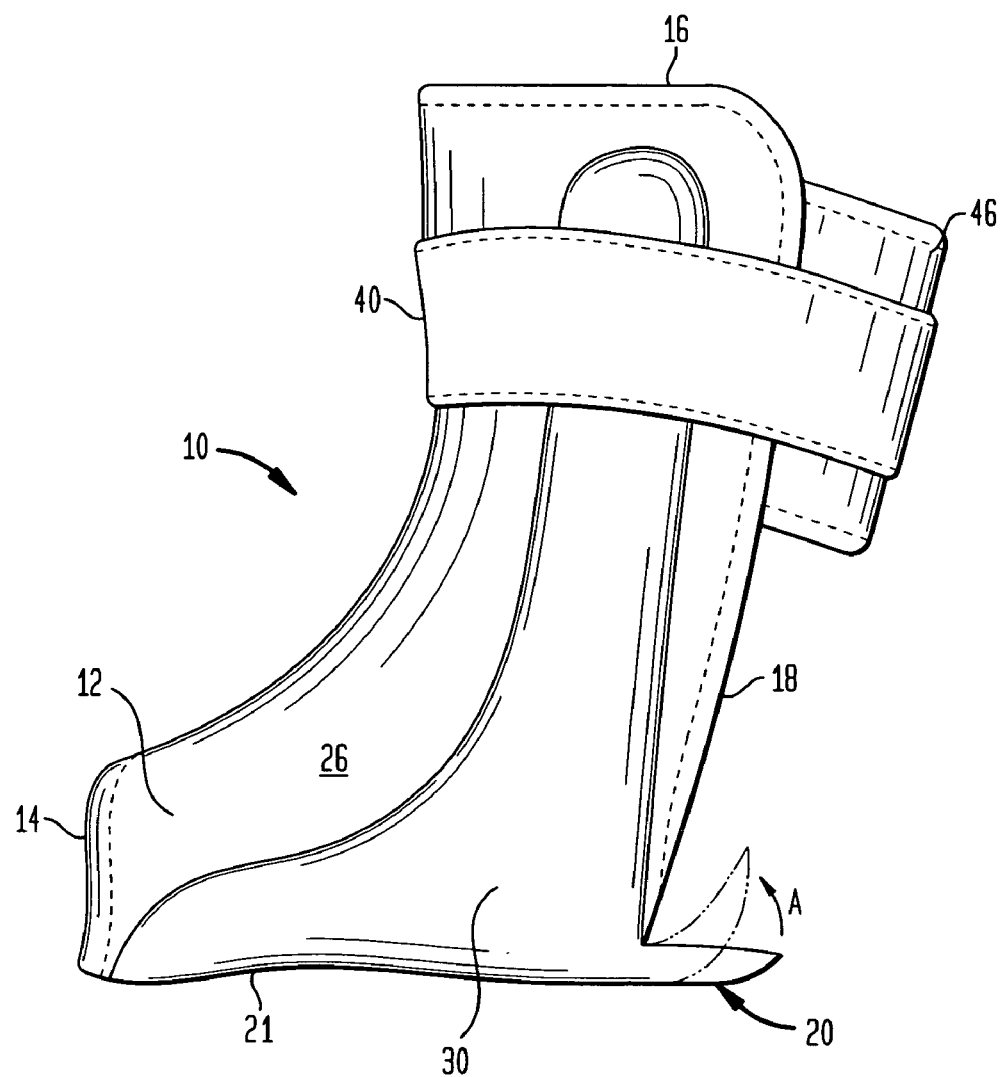
FIG. 2 is a medial side view of the ankle brace of FIG. 1.

As can be seen in FIG. 2, the ankle brace 10 and rigid member 30 form a footbed 21 which is sized to extend along the bottom of a foot from the ball of the foot, under the arch of the foot, to forward of the heel. The rigid support member 30 extends up the sides of the body 12 to support the inner and outer surfaces of the ankle and lower leg of an individual. The rigid support member 30 is formed of a rigid or semi-rigid material such as plastic.

As can be further seen in FIG. 2, the body 12 has a foot portion with forward edge 14, and a leg portion with a top edge 16 and rear edge 18. The bottom of the foot portion forms footbed 21. The footbed 21 includes a flexible heel 20 to facilitate walking. Flexible heel 20 can bend in the direction of arrow A when the user of the ankle brace is walking. Outer layer 26 extends over rigid support member 30, and also forms the bottom of the flexible heel. Strap 40, along with leg cover 46, secures the brace about a user's foot, ankle, and leg.

Figure 3:
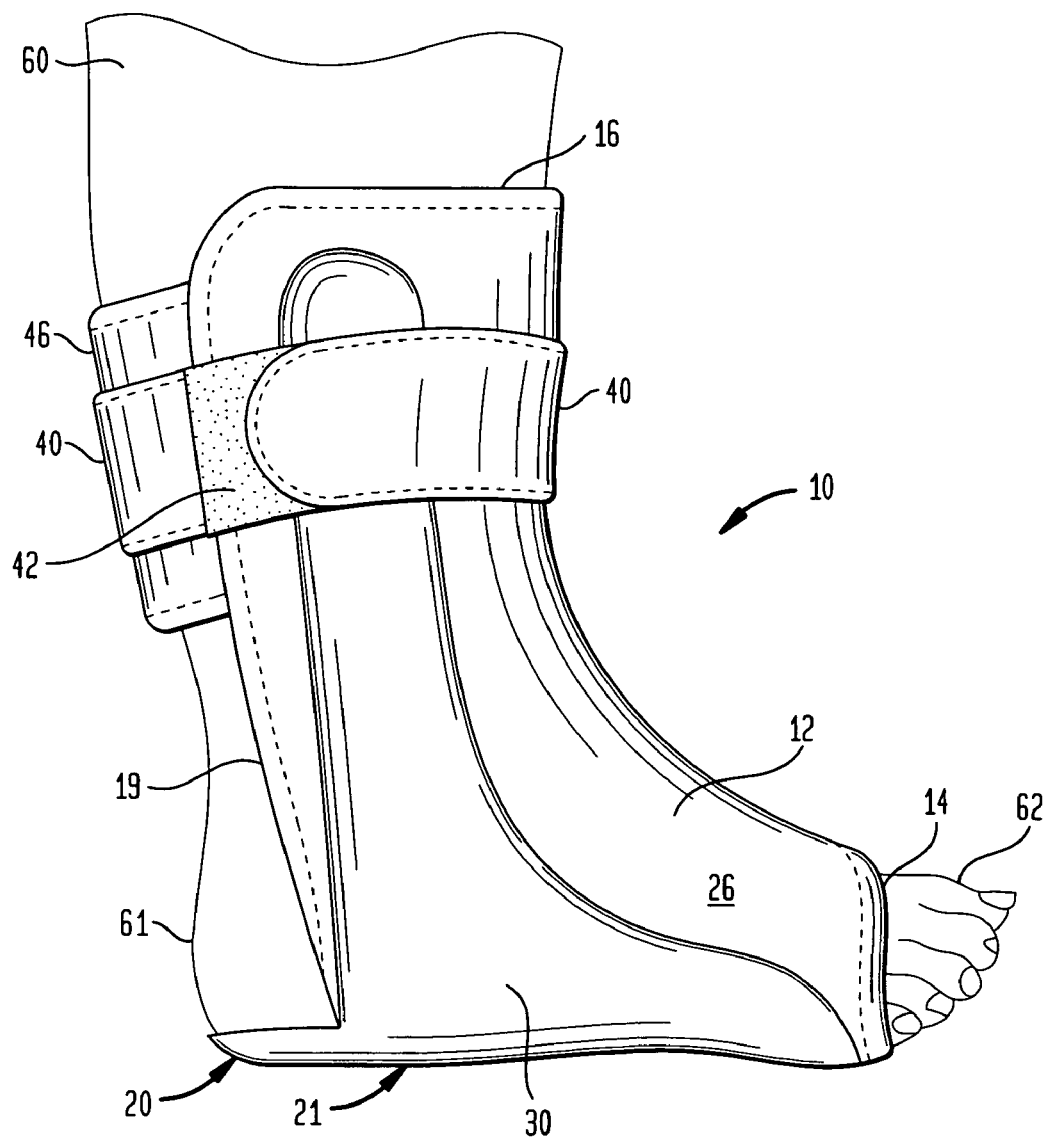
FIG. 3 is a lateral side view of the ankle brace of FIG. 1 positioned on a foot.

FIG. 3 shows the ankle brace 10 on a foot. The foot portion of body 12 surrounds the foot and ankle. Toes 62 extend past open end 14. The bottom of the foot sits on footbed 21. The leg portion covers the front of the lower leg. Upper edge 16 is positioned on leg 60. Rear edge 19 extends between the upper edge 16 and heel 20, leaving the back of the heel 61 as well as portions of the back of the leg 60 uncovered by the brace 10. The rigid support member 30 extends under the foot and up the sides of the body 10, along the ankle and lower leg, and is covered by outer layer 26.

Strap 40 and leg cover 46 wrap about the leg to retain the brace on the leg. The strap can be fastened in any known way such as with a hook and loop fastening system. One of the hook or loop elements 42 is positioned on one end of one side of the strap, and the other of the hook and loop fastening system is on the end and other side of the strap.

Figure 4:
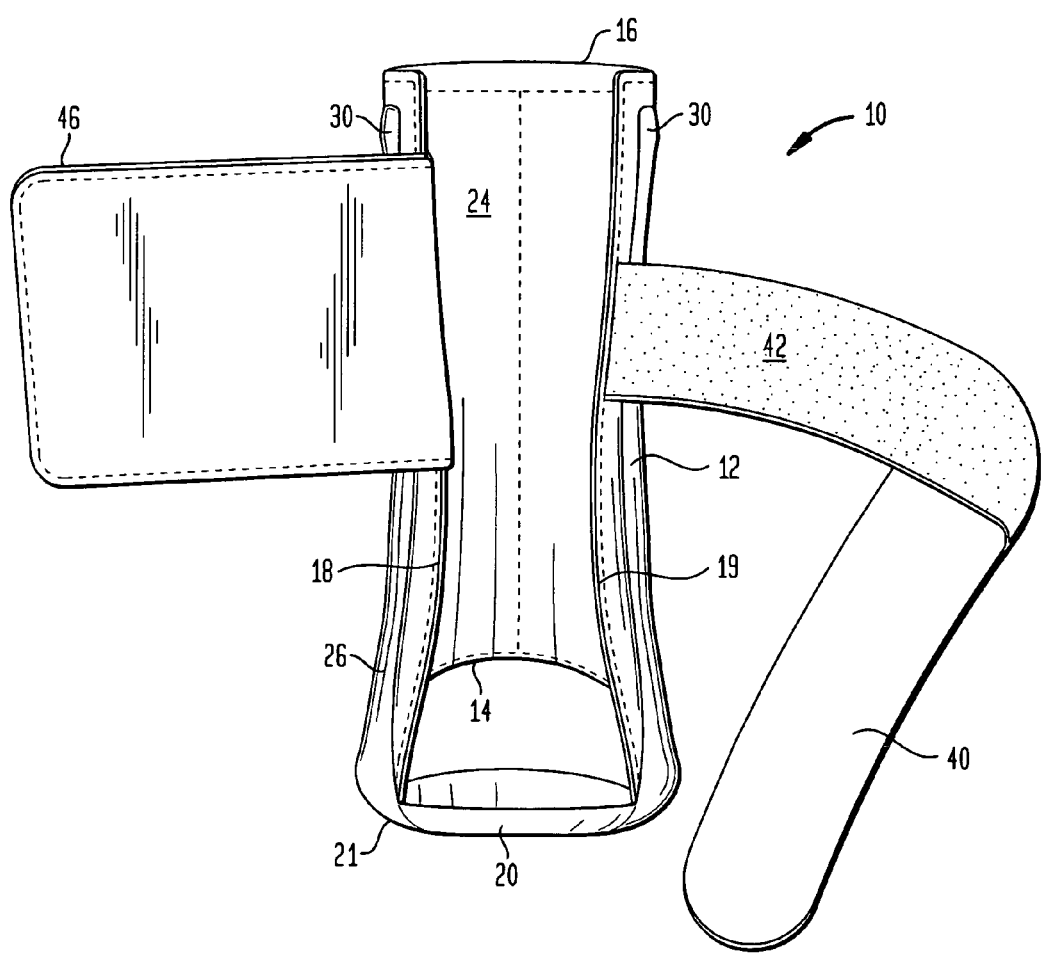
FIG. 4 is a rear view of the ankle brace of FIG. 1.
Figure 5:
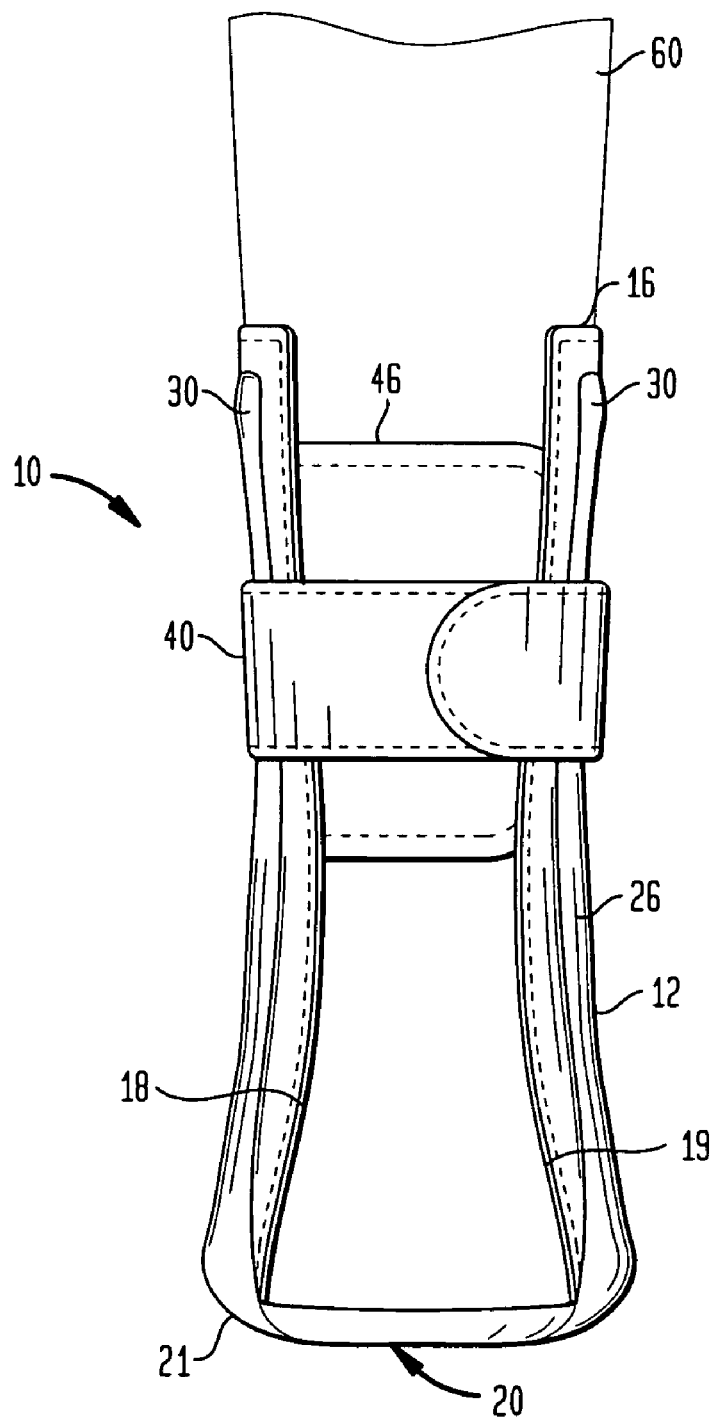
FIG. 5 is a rear view of the ankle brace of FIG. 1 positioned on a foot.

FIGS. 4 and 5 are rear views of the brace 10. Inner and outer layers 24 and 26 can be seen, and the rigid member 30 is positioned between the inner and outer layers 24 and 26. Rear edges 18 and 19 extend along the leg portion of body 12 from the footbed 21 at the heel 20 to upper edge 16. Leg cover 46 wraps about the leg, and is tucked under edge 19, and strap 40 extends over the cover about the body and is fastened on itself to hold the brace on the foot and leg, as can be seen in FIG. 5.

While a leg cover is not required, it adds comfort to the brace by dissipating the force of the strap when the strap is tightened and secured against the wearer's leg. The leg cover can be securely attached at one end, such as by sewing, onto the body of the brace. It can be attached to the inner layer of the body adjacent to an edge of the open back. It can be made of any suitable material, preferably the same material as the inner and outer layers. The leg cover is positioned over the back of the leg where the securing strap is located. When the brace is applied to the foot and leg, the end of the cover overlaps the opposite edge of the open back of the body of the brace. The strap is then wrapped about the leg over the leg cover and secured. Accordingly, the leg cover protects the leg from the strap.

Figure 6:
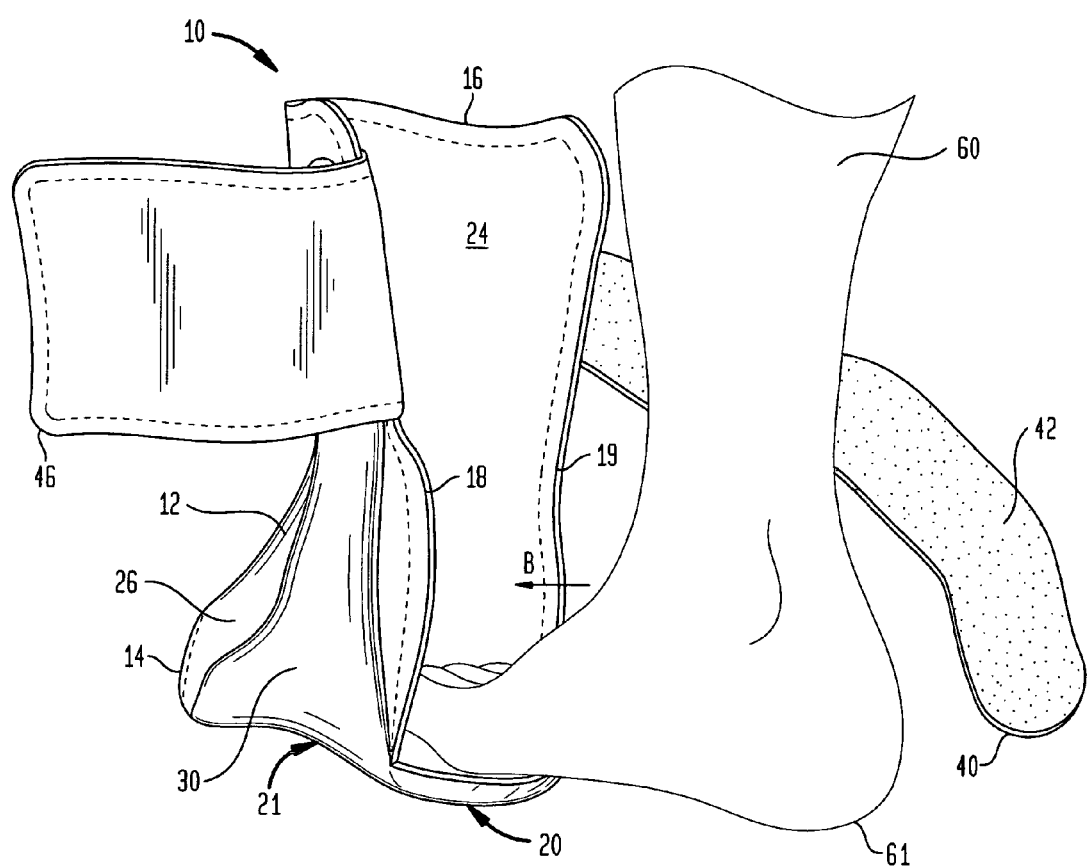
FIG. 6 is a rear perspective view of the ankle brace of FIG. 1 showing a foot entering the rear of the brace.

As shown in FIG. 6, the ankle brace 10 is placed on a foot by inserting the foot, toes first, in the direction of arrow B, through the open back of the body 12 defined by the rear edges 18, 19. The toes 62 of the foot are inserted through the open toe of brace 10 so that the foot is in the foot portion of the body 12. The sole of the foot and heel 61 are placed onto the footbed 21 and flexible heel 20. The inner layer 24 bears against the foot, ankle and lower leg, while outer layer 26 can be seen on the exterior. The strap 40 and leg cover 46, if present, are wrapped about the leg 60 and fastened. The rigid member 30 extends under the foot and up along the ankle, and lower leg. The ankle brace is worn on the leg for a time sufficient to treat the injury, or for as long as stabilization of the ankle and leg is required.

Figure 7:
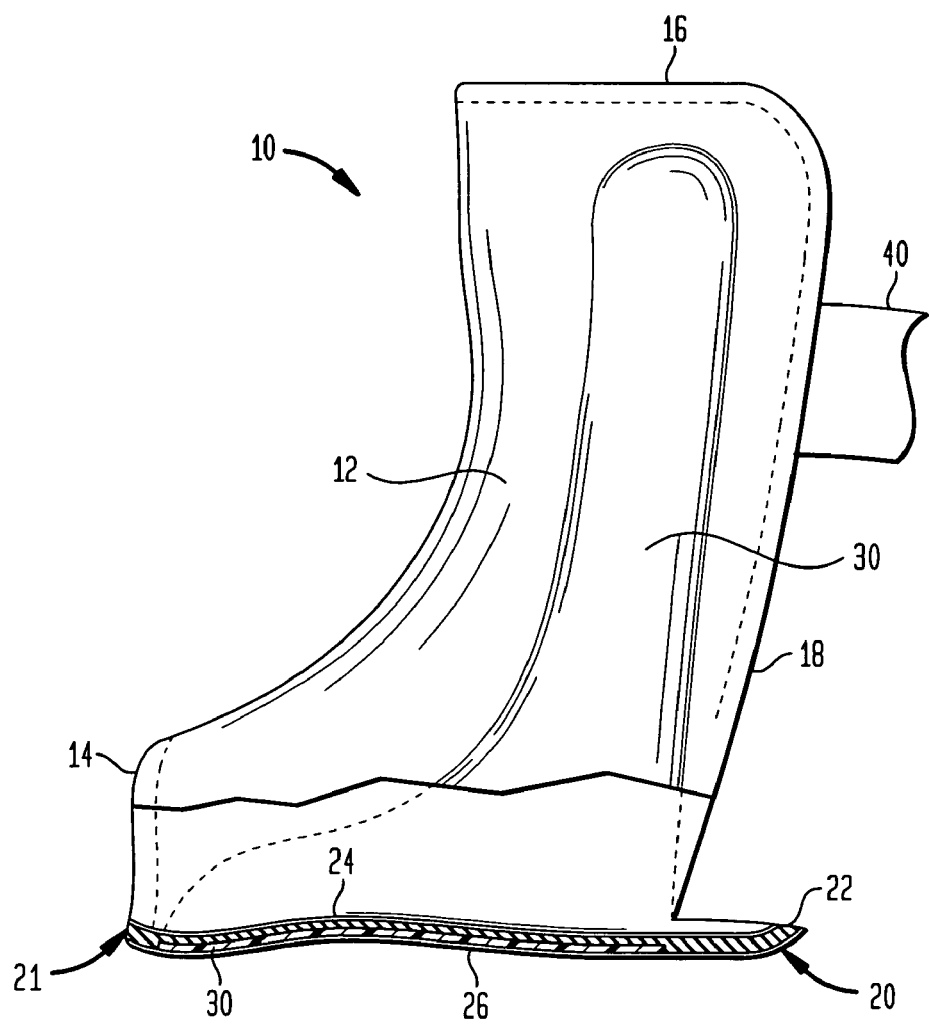
FIG. 7 is a partial cross-section view of the ankle brace of FIG. 1 showing the layers comprising the foot portion.

A cross-sectional view of the footbed 21 of the ankle brace 10 is shown in FIG. 7. As can be seen, the body 12 includes footbed 21 which comprises an outer layer 26, rigid member 30, cushion layer 22, and inner layer 24. Cushion layer 22 is positioned between the inner layer 24 and the rigid member 30. Cushion layer 22 extends from the forward edge 14 to the rear edge of the flexible heel 20. Outer layer 26 covers the bottom of the rigid member 30. The rigid member 30 extends from proximate the forward edge 14 to adjacent the flexible heel 20. The flexible heel 20 comprises inner layer 24, outer layer 26, and cushion layer 22.

Because the ankle brace provides for rear entry, it is easy to put the brace on the foot and lower leg. Because the front and sides of the brace are uninterrupted, the brace provides for better control of the forefoot and ankle. As the foot is placed in the brace, the ankle slides into proper position, and is controlled by the medial and lateral portions of the rigid support.

The rigid support member comprises a rigid or semi-rigid material such as plastic. Any suitable material, such as a thermoplastic, can be used. The rigid support member can be molded to the shape of an individual's foot and ankle to provide a custom fit to meet the individual's treatment or stabilization needs. This custom-fitted molding can be performed prior to manufacturing the ankle brace for a patient. A cast of the injured foot is taken and filled with plaster to make a positive model. The plaster model is smoothed and shaped and then the brace is molded over the model. The plastic is heated and becomes more fluid. After it is cooled, the cast is cut off and shaped to the appropriate trim lines. This type of molding process is well known in the art.

The flexible heel leaves a portion of the back of the heel of the foot unsupported by the rigid member. This flexibility, along with the open toe, provides for a more normal and anatomical gait and also allows the brace to be comfortably worn with standard footwear because there is less bulk in the rear and front of the brace. The brace may be worn with or without socks or stockings under or over the brace.

The inner and outer layers encasing the U-shaped support member and forming the boot-shaped body comprise a soft durable material such as leather; however, imitation leather, vinyl or other suitable materials can also be used. The inner and outer layers, as well as cushion layer and the rigid member, can be attached together by an adhesive. A polyadhesive, such as BARGE, has worked successfully. Additionally, the inner and outer layers can be stitched along on the edges of the brace, and at other locations, to reinforce their attachment.

The cushion layer provides a more comfortable fit to the individual by creating a soft barrier between the rigid support member and the individual's foot. The cushion layer may also be positioned between the inner and outer layers in portions of the brace other than areas where the support member extends to provide overall comfort to the individual wearing the brace. The cushion layer can comprise foam, gel, fiber or non-fiber padding, air bladder or other similar material. An example of suitable foam is a polyethylene closed cell foam such as PLASTAZOTE®, a trademark owned by ZOTEFOAMS, PLC., Surrey, England.

The strap can utilize hook and loop fasteners, buckles or other fastening means. For example, loop material can be provided on the outer side of the end portion of the end of the strap attached to the body, and hook material can be provided on substantially all of the inner side of the strap or only on the inner side of the end portion of the other end of the strap. The strap can be a separate element or can be securely attached, such as by sewing, onto the body of the brace. Preferably the strap is attached to the outer layer of the body adjacent to an edge of the open back in the calf region. The strap can be made of plastic, elastic, leather, cloth, vinyl or other suitable material. Preferably, the strap is made of the same material as the inner and outer layers. If desired, more than one strap may be provided.

The following example illustrates the present invention, but is not meant to limit its scope.

EXAMPLE

The ankle brace of the invention was tested on approximately 102 patients having the following conditions: 72 had posterior tibialis tendon dysfunction, 10 had Charcot ankles, 12 had Achilles injuries, and 8 had chronic ankle instability. The age range of the patients was 14 to 82 years with a mean age of 50. The patients were each fitted with a custom-molded ankle brace of the present invention. The patients wore the braces for approximately 12 hours per day. Patients were examined between 3 to 9 months (mean range 6 months), beginning from the time of first wearing the ankle brace of the present invention. The patients were asked questions about the status of their condition. All but two of the patients showed significant improvement in pain.

Approximately 90% of the patients were successfully treated and did not require surgical intervention.

Various details of the invention may be changed without departing from its scope. Furthermore, the foregoing description of the preferred embodiment of the invention and the example are provided for the purpose of illustration only and not for the purpose of limitation, the invention being defined by the claims.

What is claimed is:

1. An ankle brace comprising:
   a rigid U-shaped member sized to fit under a foot, the rigid U-shaped member having medial and lateral elements for extending along medial and lateral sides of a leg to support the inner and outer surfaces of an ankle and leg of an individual;
   inner and outer layers surrounding the rigid member and forming a body having a foot portion with a forward edge defining a toe aperture, and a footbed, and a leg portion with an upper edge, and rear edges extending from the upper edge to the footbed, the body having side areas adjacent the medial and lateral elements of the U-shaped member and, a flexible front area;
   a flexible heel portion that extends rearward of the intersection of the rear edges of the leg portion and the footbed; and
   a fastening strap connectable about the body to retain the brace on the foot, ankle and leg of an individual.

2. The ankle brace of claim 1 wherein the footbed is sized to extend from the ball of the foot to the heel portion of a foot.

3. The ankle brace of claim 1 wherein the flexible heel portion comprises inner and outer layers and a cushion layer therebetween.

4. The ankle brace of claim 3 wherein the cushion layer comprises foam.

5. The ankle brace of claim 1 further comprising a leg cover attached adjacent to a rear edge of the body for protecting the leg from the fastening strap.

6. The ankle brace of claim 1 further comprising a cushion layer between the inner layer and the rigid member.

7. The ankle brace of claim 6 wherein the cushion layer comprises foam.

8. The ankle brace of claim 1 wherein the fastening strap is secured about the body by a hook and loop fastening system.

9. The ankle brace of claim 1 wherein the inner and outer layers of the body comprise leather.

10. The ankle brace of claim 1 wherein the rigid member comprises plastic.

11. An ankle brace comprising:
    a foot engaging portion for receiving a foot in the form of a foot cover including a footbed, a forward edge, and a flexible heel;
    a leg engaging portion extending from the foot engaging portion, the leg engaging portion in the form of a leg cover including a top edge and rear edges extending from the top edge towards the footbed defining an opening;
    the flexible heel extending rearward of the intersection of the rear edges of the leg cover and the footbed;
    a rigid support member in the footbed and extending from proximate the forward edge to the flexible heel, the rigid member further extending up the leg engaging portion for positioning along the medial and lateral sides of a leg to support the inner and outer surfaces of the ankle and lower leg of an individual; and
    means for retaining the rear edges of the leg engaging portion in proximity to secure the ankle brace about the foot, ankle and lower leg of an individual.

12. The ankle brace of claim 11 wherein the foot engaging portion and the leg engaging portion comprise a soft durable material which encases the rigid member.

13. The ankle brace of claim 12 wherein the soft durable material comprises an inner layer which lines the interior surface of the foot engaging portion and the leg engaging portion, and an outer layer which covers the exterior surface of the foot engaging portion and the leg engaging portion.

14. The ankle brace of claim 11 further comprising a cushion layer between the inner layer and the rigid member.

15. The ankle brace of claim 14 wherein the cushion layer comprises foam.

16. The ankle brace of claim 11 wherein the flexible heel portion comprises inner and outer layers of soft durable material and a cushion layer therebetween.

17. The ankle brace of claim 11 wherein the means for retaining the rear edges in proximity comprises an adjustable strap.

18. The ankle brace of claim 17 wherein the strap secures the brace to a leg by a hook and loop fastening system.

19. The ankle brace of claim 11 wherein the leg engaging portion comprises a flexible forward portion.

* * * * *